United States Patent [19]
Junghans

[11] 3,990,956
[45] Nov. 9, 1976

[54] ELECTROCHEMICAL REDUCTION OF α,β-UNSATURATED KETO STEROIDS

[75] Inventor: Klaus Junghans, Berlin, Germany

[73] Assignee: Schering Aktiengesellschaft, Berlin & Bergkamen, Germany

[22] Filed: Jan. 14, 1975

[21] Appl. No.: 540,894

[30] Foreign Application Priority Data

Jan. 16, 1974 Germany............................ 2402482

[52] U.S. Cl. ............................ 204/59 R; 204/73 R
[51] Int. Cl.² ........................................... C25B 3/04
[58] Field of Search ........................ 204/59 R, 73 R

[56] References Cited
UNITED STATES PATENTS 3,444,057  5/1969  Throop ............................ 204/59 R
3,876,514  4/1975  Baiger ............................... 204/59 R Primary Examiner—F.C. Edmundson
Attorney, Agent, or Firm—Millen, Raptes & White

[57] ABSTRACT

A process for the preparation of keto steroids by electrochemical reduction, comprising electrolyzing a α,β-unsaturated keto steroid in a nonaqueous nitrogen-containing solvent containing an electrolyte which is at least one of:

a. a quaternary ammonium salt of the general formula $NR_1R_2R_3R_4X$, wherein $R_{1=4}$ represent an alkyl, aryl, or aralkyl residue, or b. an alkali or alkaline earth salt of X, wherein X is sufficient anion for charge equalization and represents halogen, tetrafluoborate, sulfate, perchlorate, alcoholate, arylsulfonate or alkylsulfonate.

10 Claims, No Drawings

ELECTROCHEMICAL REDUCTION OF A,B-UNSATURATED KETO STEROIDS

BACKGROUND OF THE INVENTION

This invention relates to the preparation of keto steroids from α,β-unsaturated keto steroids.

α,β-Unsaturated keto steroids within the scope of this invention are understood to mean those steroids having at least one double bond in conjugation to a keto group, such as, for example, $\Delta^4$-3-keto, $\Delta^1$-3-keto, $\Delta^{1,4}$-3-keto, $\Delta^8$-11-keto, steroids.

The term "steroid" is to be used in its broadest sense, e.g. derivatives based on the cyclic ring system known as perhydro-1,2-cyclopentanophenanthrene. It includes, for example, those steroids mentioned in "Steroids", Fieser and Fieser, Reinhold, New York, 1959. In view of the continuing research in this area, it would not be possible nor would it be necessary for the purposes of this invention, to catalog all the different types of steroids that are known.

A conventional reaction for the reduction of α,β-unsaturated ketones is the metal ammonia reduction, "Steroid Reactions, An Outline for Organic Chemists", Djerrassi, Holden-Day Inc., San Francisco, 1963, pages 299–315. This reaction is less than totally satisfactory for several reasons — one reason being that it is necessary to handle potentially dangerous elemental alkali metal, and another reason being the production of a mixture of stereoisomers instead of one product.

It is also known that the electrochemical reduction of α,β-unsaturated keto steroids in aqueous alcohol leads to the corresponding pinacols not to the corresponding saturated keto steroids (A. Kabasakalian et al, J. Amer. Chem. Soc. 78, 5032 [1956]; H. Lund, Acta Chem. Scand. 11, 283 [1957]; p. Bladon et al, J. Chem. Soc. 1958, 863; P. Bladon et al, ibid. 1962, 2352; P. Kabasakalian et al, J. Elektrochem Soc. 105, 261 [1958]; P. Zumann, ibid. 105, 758 [1956]).

SUMMARY OF THE INVENTION

An object of this invention is to provide a new process for converting α,β-unsaturated keto steroids selectively to the corresponding keto steroids.

Another object is to provide novel reaction media such as electrolysis solutions.

Upon further study of the specification and appended claims, further objects and advantages of this invention will become apparent to those skilled in the art.

These objects are attained by electrolyzing α,β-unsaturated keto steroids in the presence of a quaternary ammonium salt of the general formula $NR_1R_2R_3R_4X$, wherein $R_{1-4}$ represent an alkyl, aryl, or aralkyl residue, and X represents an anion necessary for charge equalization, or in the presence of an alkali or alkaline earth salt with the anion X, wherein X represents, for example, halogen, tetrafluoborate, sulfate, perchlorate, alcoholate, or arylsulfonate and alkylsulfonate, in a nonaqueous nitrogen-containing solvent, optionally with the addition of solubilizer means.

It was expected that only the double bond in conjugation with the keto group is reduced when the aqueous system of the prior art is replaced by the nonaqueous system of this invention.

Furthermore, it could not be expected, either, that the reduction of the $\Delta^4$-double bonds in the α,β-unsaturated-steroids would not result in a mixture of stereoisomers, but rather in a stereochemically unitary product.

DETAILED DISCUSSION

The electrolysis can be conducted in a divided or undivided cell. The process is preferably effected in an undivided cell. It is possible to use alternating current, rectified, unsmoothed alternating current, direct current, or modulated direct current. The electrolysis conditions, such as voltage, amperage, current density, electrode surface, as well as pressure and temperature, can be varied within wide limits. Preferably, the electrolysis is carried out at a current density of 0.01 – 1A/cm² (ampere per square centimeter). The temperature range of the electrolysis is between −50° C. and the boiling temperature of the solvent or solvent mixture, preferably being between 0° C. and 50° C. The chemical composition of the electrode material is not critical, it being sufficient that the electrode is capable of conducting current and is stable under the conditions of electrolysis. Examples of electrode materials include, but are not limited to: nickel, aluminum, gold, iron, lead, graphite, or platinum. The electrolytic reaction can be conducted continuously or discontinuously.

Of the nonaqueous, nitrogen-containing solvents, preferred are liquid ammonia and amines of low molecular weight, i.e., having not more than 8 carbon atoms, for example, methyl-, ethyl-, or propylamine, ethylenediamine, 1,3-propanediamine, etc., individually or in mixtures with one another. Hexamethylphosphoric triamide by itself is also very suitable as the solvent. The solvent must be inert with respect to the reactants and products under conditions of the reduction. Aside from the aforementioned solvents, others include but are not limited to aliphatic and cycloaliphatic amines and acid amines, e.g., piperidine, cyclohexyl amine, morpholine and tetramethylurea. It is clear that these solvents are not merely non-aqueous solvents containing dissolved nitrogen, but instead the solvent must be a nitrogen compound, e.g. ammonia, an amine or amide.

To increase the solubility of the steroids and/or to raise the conductivity per se, it is possible to add still further solvents to the electrolysis solution. Examples are aliphatic or cycloaliphatic ethers, such as diethyl ether, tetrahydrofuran, and dioxane, acid derivatives, such as dimethylformamide, hexamethylphosphoric triamide, acetonitrile, propylene carbonate, sulfolane, pyrrolidone, hydrazine, aromatic amines, such as aniline or mono- and dimethyl aniline. Such additional solvents are herein characterized as "solubilizer means". Any of these "solubilizer means" which are nonaqueous nitrogen-containing solvents can be also used as solvent without further "solubilizer means".

To conduct the process of this invention, an electrolyte salt must be present in the electrolysis solution. Preferred electrolyte salts are quaternary ammonium salts of the general formula $NR_1R_2R_3R_4X$, wherein $R_{1-4}$ represent any alkyl, aryl, or aralkyl residue which does not interfere with the reaction. Preferred residues are hydrocarbyl, for example, methyl, ethyl, propyl, butyl, phenyl, tolyl, and benzyl. The anion X necessary for charge equalization is such that it does interfere with the reaction, and is preferably halogen, such a fluorine, chlorine, bromine, or iodine. Likewise suitable are complex anions, including but not limited to: tetrafluoborate, sulfate, perchlorate, alcoholates of lower alcohols, such as methylate or ethylate, or aryl- and alkylsulfonates. Especially preferred quaternary ammonium salts are: tetraethylammonium p-toluenesulfonate, tetrabutylammonium perchlorate, triethylbutylammonium bromide, tetrapropylammonium iodide, tetraheptylammonium tetrafluoborate and tetramethylanilinium iodide.

Additional preferred electrolytes are alkali or alkaline earth salts with the anion X, for example, LiCl, NaBr, KI, RbF, Cs $BF_4$, $(Sr)_2SO_4$, $Mg(OCH_3)_2$, $Ca(OC_2H_5)_2$, $Ba(ClO_4)_2$ and $Sr(C_6H_5SO_3)_2$. The function of the electrolyte is to transport charge between the electrodes.

The concentration of the electrolyte salt and the steroid to be reduced is not significant to the success of the reduction and can be varied within wide limits. Accordingly, the reduction is not adversely affected by the fact that part of the substances is present in the solid phase (saturated solution).

The electrochemical reduction of the double bond in conjugation to a keto group takes place relatively quickly and is completed, for example, at room temperature and a current density of 0.5 $A/cm^2$, within about 15 minutes. Non-conjugated keto groups, such as the 11 and 20 -keto groups, and other double bonds, such as the $\Delta^{16}$-double bond, are concomitantly reduced in the same period of time.

Once the double bond is reduced, the keto group is no longer conjugated. Accordingly, if the electrolysis is continued, for example, the period more than doubled, the previously conjugated keto group is also reduced to the hydroxy group. Accordingly, the reaction is monitored by conventional methods so that it can be terminated at the desired time.

The process of this invention has the advantage that the expenditure for apparatus is relatively low, and the electrolysis can be effected in a short period of time. Furthermore, the reduction is substantially independent of temperature and pressure. Still further, the process is safe in operation as compared to known processes for the reduction of steroids, since, for example, the step of working with elemental alkali metals is eliminated.

The starting steroids usable for the process of the present invention are defined in the "Background of the Invention", and can thus contain, in addition to the double bond in conjugation to a keto group, for example, still other exocyclic or ring non-conjugated keto groups on the steroid molecule, which are reduced simultaneously with the double bond. Such non-conjugated keto groups can be present, for example, in the 11-, 17-, or 20-position in the steroid molecule. Furthermore, it is to be understood that the expression $\alpha,\beta$-unsaturated keto steroid not only means that the keto group is in conjugation with only one double bond, but also means that the keto group can be in conjugation with two double bonds, such as, for example, in case of a 3-keto-$\Delta^{1,4}$ or 3-keto-$\Delta^{4,6}$ steroids.

The $\alpha,\beta$-unsaturated keto steroids used as the starting compounds can moreover contain further, unreducible substituents, such as, for example, alkyl groups, especially methyl groups in the 1-, 2-, 4-, 6-, 7-, 10-, 13-, or 16-position, and free or etherified or esterified hydroxy groups in the 1-, 6-, 7-, 11-, 15-, 16-, or 17-position. A 17-alkyl group can be in the $\alpha$- or $\beta$-configuration.

The compounds produced according to this invention are either intermediates for the preparation of known pharmaceuticals or are themselves known pharmaceuticals. Thus, it is possible, for example, to obtain from 5$\alpha$-androstan-17$\beta$-ol-3-one, by bromination in the 2-position, dehalogenation in the presence of calcium carbonate/lithium bromide under heating and methylation, e.g., with lithiumdimethylcopper, the conventional 1-methyl-5$\alpha$-androst-1-en-17$\beta$-ol-3-one (methenolone).

An example for a valuable drug which can be directly produced according to the process of this invention is the conventional 1$\alpha$-methyl-5$\alpha$-androstan-17$\beta$-ol-3-one (mesterolone).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

0.5 g. of testosterone is electrolyzed in 100 ml. of methylamine with 2.5 g. of lithium chloride between two platinum electrodes at a current density of 0.05 $A/cm^2$ for 10 minutes. After the solvent has been evaporated, the residue is combined with water and filtered. Recrystallization from ethyl acetate yields 0.4 g. of 5$\alpha$-androstan-17$\beta$-ol-3-one, m.p. 175°C.

EXAMPLE 2

0.50 g. of testosterone is electrolyzed in 100 ml. of liquid ammonia with 0.2 g. of sodium chloride between a nickel cathode and a graphite anode for 1 hour at 0.5 A. After the reaction mixture has been worked up as described in Example 1, recrystallization yields 0.32 g. of 5$\alpha$-androstan-17$\beta$-ol-3-one, m.p. 169.5°–170.5° C.

EXAMPLE 3

0.50 g. of nortestosterone is electrolyzed in 100 ml. of methylamine with 2.5 g. of lithium chloride between two platinum electrodes at a current density of 0.1 $A/cm^2$ for 15 minutes. After the reaction mixture has been worked up and recrystallized, 0.41 g. of 5$\alpha$-estran-17$\beta$-ol-3-one is obtained, m.p. 140°–141° C.

EXAMPLE 4

0.50 g. of 1$\alpha$-methyltestosterone is electrolyzed in 100 ml. of methylamine with 4 g. of tetraethylammonium p-toluenesulfonate between two platinum electrodes at 0.5 A for 15 minutes. The reaction mixture is worked up; recrystallization yields 0.38 g. of 1$\alpha$-methyl-5$\alpha$-androstan-17$\beta$-ol-3-one, m.p. 202.5°–203.5° C.

EXAMPLE 5

0.10 g. of androsta-1,4-diene-3,17dione is electrolyzed in 100 ml. of methylamine with 2 g. of lithium chloride between two platinum electrodes at a current density of 1 $A/cm^2$. The reaction mixture is worked up, and recrystallization yields 0.04 g. of 5$\alpha$-androstan-17$\beta$-ol-3-one, m.p. 174.5° – 175.5° C.

EXAMPLE 6

0.50 g. of androst-4-ene-3,17-dione is dissolved in 10 ml. of tetrahydrofuran and electrolyzed in 100 ml. of methylamine with 0.5 g. of lithium chloride for 1 hour between a platinum cathode and a tungsten carbide anode at 0.5 A. After the reaction mixture has been worked up and recrystallized, 0.38 g. of 5α-androstan-17β-ol-3-one is obtained, m.p. 172.5° – 173.5° C.

EXAMPLE 7

0.50 g. of 1α-methylandrost-4-ene-3,17-dione is dissolved in 20 ml. of dimethylformamide and electrolyzed in 100 ml. of ammonia with 0.5 g. of sodium perchlorate for 1 hour between two graphite electrodes at a current density of 0.5 A/cm$^2$. The mixture is worked up; recrystallization yields 0.35 g. of 1α-methyl-5α-androstan-17β-ol-3-one, m.p. 205° – 208° C.

EXAMPLE 8

0.50 g. of 1α-methyltestosterone is electrolyzed in 100 ml. of liquid ammonia in the presence of 1 g. of sodium ethylate between an aluminum cathode and a graphite anode for 15 minutes at 0.5 A/cm$^2$. The reaction mixture is worked up, and recrystallization yields 0.35 g. of 1α-methyl-5α-androstan-17β-ol-3-one, m.p. 201.5° – 203° C.

EXAMPLE 9

0.50 g. of pregna-4,16-diene-3,20-dione is electrolyzed in 100 ml. of ammonia with 0.5 g. of llithium chloride at 1 A between a gold cathode and a graphite anode for 1.5 hours. The mixture is worked up. Recrystallization yields 0.42 g. of pregnan-20-ol-3-one, m.p. 182° – 183° C.

EXAMPLE 10

0.50 g. of testosterone is electrolyzed in 100 ml. of ammonia with 1 g. of sodium chloride between an aluminum cathode and a graphite anode for 2.5 hours at 1 A. The mixture is worked up and recrystallized, yielding 0.38 g. of 5α-androstane-3β, 17β-diol, m.p. 164° C.

EXAMPLE 11

0.5 g. of 5α-androst-1-en-17β-ol-3-one in 20 ml. of tetrahydrofuran is reacted in 150 ml. of ammonia for 15 minutes at 0.2 A/cm$^2$ in a divided cell with the use of sodium chloride as the conductive salt and a gold cathode and an anode of glass-like carbon. After the catholyte has been worked up and the crude product has been recrystallized, 0.38 g. of 5α-androstan-17β-ol-3-one is obtained, m.p. 173° – 175° C.

EXAMPLE 12

0.5 g. of 3-methoxy-1,3,5(10), 8-estratetraen-17β-ol-11-one in 30 ml. of tetrahydrofuran is reacted in 150 ml. of ammonia for 20 minutes at 0.05 A/cm$^2$ in a divided cell with the use of sodium chloride as the conductive salt and with two electrodes of glass-like carbon. After the catholyte has been worked up and the crude product has been recrystallized, the yield is 0.35 g. of 3-methoxy-1,3,5(10)-estratrien-17β-ol-11-one, m.p. 179° – 181° C.

EXAMPLE 13

0.5 g. of Δ$^8$-22a-5α-spirosten-3β-ol-11-one in 40 ml. of tetrahydrofuran is electrolyzed in liquid ammonia for 15 minutes at 0.1 A/cm$^2$ in a divided cell with the use of lithium chloride as the conductive salt and two platinum electrodes. After the catholyte has been worked up and the crude product has been recrystallized, 0.3 g. of 22a-spirostan-3β-ol-11-one is produced, m.p. 221° – 225° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of α,β-saturated keto steroids by electrochemical reduction, comprising electrolyzing a α,β-unsaturated keto steroid to saturate the α,β position while not reducing the conjugated keto group, said electrolyzing being conducted in an inert nonaqueous solvent, said solvent being ammonia, an amine or an amide, said solvent containing an electrolyte which is at least one of:
   a. a quaternary ammonium salt of the general formula NR$_1$R$_2$R$_3$R$_4$X, wherein R$_{1-4}$ represent an alkyl, aryl, or aralkyl residue, or
   b. an alkali or alkaline earth salt of X, wherein X is sufficient anion for charge equalization and represents halogen, tetrafluoborate, sulfate, perchlorate, alcoholate, arylsulfonate or alkylsulfonate,
and discontinuing said electrolyzing before the resultant previously conjugated keto group is reduced substantially to the hydroxy group.

2. A process according to claim 1 wherein the nitrogen-containing solvent is a solvent of the group of organic acid amides, aliphatic and cycloaliphatic amines.

3. A process according to claim 1 wherein the electrolysis is conducted at a current density of 0.01 – 1 A/cm$^2$ and at a temperature of 0 – 50° C.

4. A process according to claim 1 wherein the electrolyte is said quaternary ammonium salt.

5. A process according to claim 1 wherein the electrolyte is said alkali metal salt of X.

6. A process according to claim 1 wherein the electroltye is said alkaline earth metal salt of X.

7. A process as defined by claim 1 wherein the α,β-unsaturated keto steroid is testosterone, nortestosterone, 1α-methyltestosterone, androsta-1,4-diene-3,17-dione, androst-4-ene-3,17-dione, 1α-methylandrost-4-ene-3,17-dione, pregna-4,16-diene-3,20-dione, 5α-androst-1-en17β-ol-3-one, 3-methoxy-1,3,5(10),8-estratetraen-17β-ol-11-one or Δ$^8$-22a-5α-spirosten-3β-ol-11-one.

8. A process according to claim 7 wherein the nonaqueous solvent is at least one of liquid ammonia, methylamine, ethylamine, propylamine, ethylenediamine, 1,3-propanediamine, or hexamethylphosphonic triamine.

9. A process according to claim 7 wherein the electrolysis is conducted at a current density of 0.01 – 1 A/cm$^2$ and at a temperature of 0° – 50° C.

10. A process according to claim 8 wherein the electrolysis is conducted at a current density of 0.01 – 1 A/cm$^2$ and at a temperature of 0° – 50° C.

* * * * *